United States Patent [19]

Yang

[11] Patent Number: 5,403,926
[45] Date of Patent: Apr. 4, 1995

[54] HEPATOCELLULAR CARCINOMA ONCOGENE

[75] Inventor: Stringner S. Yang, Bethesda, Md.

[73] Assignee: The United States of America as represented by the Department of Health and Human Services, Washington, D.C.

[21] Appl. No.: 774,156

[22] Filed: Oct. 15, 1991

Related U.S. Application Data

[63] Continuation of Ser. No. 451,953, Dec. 19, 1989, abandoned.

[51] Int. Cl.$^6$ .................... C07H 21/02; C07H 21/04; C12Q 1/68; C12N 15/00
[52] U.S. Cl. ...................................... 536/23.6; 435/6; 935/77; 935/78
[58] Field of Search ....................................... 536/23.6

[56] References Cited

PUBLICATIONS

Yang et al, Molecular Cloning of the Endogenous Rat C-type Helper Virus DNA Sequence: Structural Organization and Functional Analysis of Some Restricted DNA Fragments, Journal of General Virology, vol. 63, 1982, pp. 25–36.

ENBL Database, Accession #V01511, 1983.

Yang et al; "Transforming DNA Sequences of Human Hepatocellular Carcinomas, Their Distribution and Relationship with Hepatitis B. Virus sequence in Human Hepatomas"; Leukemia, vol, 2, No. 12; Dec. 1988; pp. 102–113.

*Primary Examiner*—Mindy B. Fleisher
*Attorney, Agent, or Firm*—Susan S. Rucker

[57] ABSTRACT

The present invention relates to an oncoprotein specific for hepatocellular carcinomas and to a nucleotide sequence that codes for such a protein. The invention further relates to screening and diagnostic methodologies (and kits based thereon) that make use of the oncoprotein (or antibodies specific for same) and the nucleotide sequence.

8 Claims, 6 Drawing Sheets

FIG. 1A

```
                                                      27                     *   54                                81
AAG CTT AAT AGA AAA TAT GAG CAA CAT ACA CAA ACA TTA GCA ACA ATG ATA TAA AAT ACC ACT TAA ACA GGA AAA ATG
                                                                                                      MET

162
TTG CCC TTC ACT TGT GGA AGA AAT GAA AAC AGC CCT AGG GAT GTT GAC GTT GGG GTG GCA CCT GCT GCA GAG GGT
Leu Pro Phe Thr Cys Gly Arg Asn Glu Asn Ser Pro Arg Asp Val Asp Val Gly Val Ala Pro Ala Ala Glu Gly

243
AAC GTG CAG CAT GTC GAG GGC AGC AAG ACT GCC AAG GCT GGT TTG AGC TCA AGG GGA GGA GGT GGA CTC TCC CAT CTC
Asn Val Gln His Val Glu Gly Ser Thr Ala Lys Ala Gly Leu Ser Ser Arg Gly Gly Gly Gly Leu Ser His Leu

324
TTC TGC AGC TCT AAA CCC TGC CTG AAA CAC GTG GAG AAG CTA TCT CCA CCA GGA CAC CAA ATG CAA ATG GAC
Phe Cys Ser Ser Lys Pro Cys Leu Lys His Val Glu Lys Leu Ser Pro Pro Gly His Gln MET Gln MET Asp

405
ACT CTG ATC ATA AAA TTA TCA GGA AGA AAT AAG ACA ATG GAG GTG CCA CCA AAC CAG TGG AAA TTT TTC CCC
Thr Leu Ile Ile Lys Leu Ser Gly Arg Leu Arg Asn Lys Thr MET Glu Val Pro Pro Asn Gln Trp Lys Phe Phe Pro

486
TTT TCA TTC CTC CAT TCC CTG GCC TTG ACT CAA GGC AGC CCA CAC TCT AGG AGC AGA CAC CAG GGC ACA GGT GGG GAG
Phe Ser Phe Leu His Ser Leu Ala Leu Thr Gln Gly Ser Pro His Ser Arg Arg His Gln Gly Thr Gly Gly Glu

567
CTC TGG GGG ACC CTC CAG GCT TAC TCA GTG AAT GGG TTA GCA GCA GCC ACA GGA GCC ATG GAG CCT GCA GGG ACC CAC
Leu Trp Gly Thr Leu Gln Ala Tyr Ser Val Asn Gly Leu Ala Ala Ala Thr Gly Ala Thr MET Glu Pro Ala Gly Thr His

648
AAC ACT GAG GGC AGG GAT CTT GCC CTT AAT CAG ATA AGC TGT GAT TCC CGA GAG GGT GGG GTA AAG GCC ACG GGT TTT
Asn Thr Glu Gly Arg Asp Leu Ala Leu Asn Gln Ile Ser Cys Asp Ser Arg Glu Gly Gly Val Lys Ala Thr Gly Leu Phe

729
CTC TCC ACA TCT TCC CAC ATG GTC ACC CCA GAG GGT CGA AGA GGG AGA AAG TGT GAG CAC CGT GAC ATA ATG AGC CGC AGC
Leu Ser Thr Ser Ser His Val MET Thr Pro Glu Gly Arg Arg Gly Arg Lys Cys Glu His Arg Asp Ile MET Ser Arg Ser
```

FIG. 1B

```
                                              756                          783                                810
CTT CTG ACT AGA TGC CCC AAA GAA GAA TCC CAG GTG ACC ACA CAG CAT CAG AGA AAC TGC AGG GTA ATG AGG AAC TTT GGA
Leu Leu Thr Arg Cys Pro Lys Glu Glu Ser Gln Val Thr Thr Gln His Gln Arg Asn Cys Arg Val MET Arg Asn Phe Gly 837                                864                                                      891
AAG CAA TCC ATC GTG TTG TCA GTA AAA CCT CTG GCT CAC CTC GGA GCT GGG CAT GCA TGG ATG GTG ACC CTC GAT GGA ATA
Lys Gln Ser Ile Val Leu Ser Val Lys Pro Leu Ala His Leu Gly Ala Gly His Ala Trp MET Val Thr Leu Asp Gly Ile 918                                947                                                      974
GAC TAT GAG GAA CCA GGT GAG ATC TAC CTC CAC CGA GAC GTG AGA GAC GTG ACC TGC ATA CCC AAA CAC CAT GAG GCT TTA
Asp Tyr Glu Glu Pro Gly Glu Ile Tyr Leu His Arg Asp Val Arg Asp Val Thr Cys Ile Pro Lys His His Glu Ala Leu 999                                1028                                                     1053
AAG ACT GAG CTG ATG TGG AAG CCA CAG CCT CTG CAG GTT GCT CTG CAC TTG CAA CAT AAG CCC AAC CAC ATC AAT TGC TGC
Lys Thr Glu Leu MET Trp Lys Pro Gln Pro Leu Gln Val Ala Leu His Leu Gln His Lys Pro Asn His Ile Asn Cys Cys 1080                               1107                                                     1134
AAA ACA CTA CAG CAT TCT CCA TAC CAC TTA AAT AAG ACA CAG AGT CTC ACA ACA TTC AAA ACG CCC AGG ACA CAA TCC
Lys Thr Leu Gln His Ser Pro Tyr His Leu Asn Lys Thr Gln Ser Leu Thr Thr Phe Lys Thr Pro Arg Thr Gln Ser 1161                               1188                                                     1215
AAA ATT ACT TCT ACA AAA ATT GGA ATC ATC AAC AAT GAG CAA AAT CTC AAT GAA ATA ATT CTC ATA AGC ATT GCT GCC AGT GCT GAG ATG ACA
Lys Ile Thr Ser Thr Lys Ile Gly Ile Ile Asn Asn Glu Gln Asn Leu Asn Glu Ile Ile Ile Ser Ile Ala Ala Ser Ala Glu MET Thr 1248                               1270                                                     1296
ATG AGG GTT GGA ATC ATC AAC AAC ATC TTT AAA GTA GTA TCA TGG CAA CAA GTA CAA GTA GCA ATG GCA AAC ACT CTT GAG ATA
MET Arg Val Gly Ile Ile Asn Asn Ile Phe Lys Val Val Ser Trp Gln Gln Val Gln Val Ala MET Ala Asn Thr Leu Glu Ile 1323                               1350                                                     1377
AAT GGA AAG ATA AGA AGG CTC AGG GAG AAA TGT ACA AAG AAT GAC CAA GTG GGA ATT GCA CCA CTG GAA ACA AAT
Asn Gly Lys Ile Arg Arg Leu Arg Glu Lys Cys Thr Lys Asn Asp Gln Val Gly Ile Ala Pro Leu Glu Thr Asn 1404                               1431                                                     1458
CAC CAG GAT AAA GCA GTC TCT GGC TGG GCC AAC AGG AGA ATG AAA AGG AGA ATG GCA GTT GTC CAA
His Gln Asp Lys Ala Val Ser Gly Trp Ala Asn Arg Arg MET Glu Arg Arg Glu MET Lys Arg Ala Val Val Gln
```

FIG. 1C

```
                                                                                        1539
                                            1512                          * ┌──────┐
           1485                                                             │ATA ATC│ CCA ATA CCT TGG
TTT GAA CAA CAC AAA AGA CAC┌───┐TTT AAA AAA AAA TGA GGC AGG GCT CAG TGG CTC ACA CCT└──────┘
Phe Glu Gln His Lys Arg His│TGA│                                             Pro Ile Pro Ile Pro Trp
                           └───┘
                                                                                        1620
           ↑     ┌───┐                1566                    1593
GAG GCC GAG GCA │ATG│ TAT CAC CTG AGG TCA GGA GTT CAA GAC TAC CCT GGC CAA CAT GGC AAA ATC CCA TCT CTA CTG AAA
                │MET│ Tyr His Leu Arg Ser Gly Val Gln Asp Tyr Pro Gly Gln His Gly Lys Ile Pro Ser Leu Leu Lys
                └───┘
                                    1647                              1674                          1701
ATA CAA GAA TTA GCT GGG CAT GGT GCT GGG AGG TGC CTG CAA TCC CAG CTA CTC AGG CTG AGG CAG GAG AAT CAC TTG AAC
Ile Gln Glu Leu Ala Gly His Gly Ala Gly Arg Cys Leu Gln Ser Gln Leu Leu Arg Leu Arg Gln Glu Asn His Leu Asn
                          1728                              1755                          1782
TCG GGA AGA GGG TGC AGT GAG GGG TGC CCA AAA TCG CAC CTC TGC ATT CCA TTA CCA GTG ACA GAG GGA GAC TCT GTC TCA AAA
Ser Gly Arg Gly Cys Ser Glu Gly Cys Pro Lys Ser His Leu Cys Ile Pro Leu Pro Val Thr Glu Gly Asp Ser Val Ser Lys
                                      1809                              1836                          1863
CAA AAC ACA GAA AAT GAA CAG CAC CTC AGG AAC AAT ACC AAA AAG TCC AAC AGC TGT ATA ATT GGT GGC CCA GAA GGA
Gln Asn Thr Lys Asn Glu Gln His Leu Arg Asn Asn Thr Lys Lys Ser Asn Ser Cys Ile Ile Gly Gly Pro Glu Gly
                          1890                              1917                          1944
GAG GAG AAA GAG TGG AGT ACA GAA ATG AGA TCT GAA GAA CTA ATG ACT GAT AAT GTT TCA ATT TTG AAA AAG GAC ATA AAC
Glu Glu Lys Glu Trp Ser Thr Glu MET Arg Ser Glu Glu Leu MET Thr Asp Asn Val Ser Ile Leu Lys Lys Asp Ile Asn
                                    1971                              1998                          1024
CTA AAG ATT ATA GAT TCA AAA GCC CAG CTG AAT TCA AAT AGG ATA GAT GCA GAT ATA TCA AAT TTA AAC TGT GAA
Leu Lys Ile Ile Asp Ser Lys Ala Gln Leu Asn Ser Asn Arg Ile Asp Ala Asp Ile Ser Asn Leu Asn Cys Glu
                          2052                              2079                          2106
ATA AAT TGG TTT TGT CAC GCA GCA CCA AAG TAC CAA GAT CAA GAT CAA AGA TAC ACA AGG AAG GAA GGA AAT ACA
Ile Asn Trp Phe Cys His Ala Ala Pro Lys Tyr Gln Asp Gln Asp Gln Arg Tyr Thr Arg Lys Glu Gly Asn Thr
                          2133         ↑              2160                          2187
GAA TAT TAT GGC CAT GGG AAA GAG GTG TCA GTG TGA ATA CAT AGA ACA CAC TTA AGC GCA AAC AAC CCC AAA TGA TGG GGC
Glu Tyr Tyr Gly His Gly Lys Glu Val Ser Val       Ile His Arg Thr Ala His Leu Ser Asn Asn Pro Lys • Trp Gly
```

HEPATOCELLULAR CARCINOMA ONCOGENE

This application is a continuation of U.S. patent application Ser. No. 07/451,953, filed Dec. 19, 1989, now abandoned.

BACKGROUND OF THE INVENTION

1. Technical Field

The present invention relates, in general, to a protein of hepatoma cells, and, in particular, to an oncoprotein that is an amplified gene expression product of hepatoma cells. The invention further relates to a nucleotide fragment coding for the oncoprotein, to a recombinant molecule that includes such a fragment and to cells transformed therewith. The invention further relates to methods of detecting the presence of hepatocellular carcinomas in a patient and to kits based thereon.

2. Background Information

Epidemiological evidence has led to a strong etiological implication of several DNA viruses with the occurrence of certain cancers and other disorders in humans. These include the papillomavirus in cervical carcinoma (HPV 16) and in epidermodysplasia verruciformis (HPV 3 and 8); the Epstein-Barr virus in Burkitt's lymphoma; and the hepatitis B virus (HBV) in human hepatocellular carcinoma (Beasley et al, In: Vyas G. N., Dienstag J. L., Hoofnagle J. H., eds. Viral hepatitis and liver disease. Orlando, Fla., Grune and Stratton, 1984, 209–224). These observations, together with the correlation of retroviral infection such as HTLV-I in Adult T-cell leukemia asserts the possible role of infectious viruses acting as transducing agents in the pathogenesis of these aforementioned human neoplasms and disorders.

The mechanism(s) by which infectious viruses exert their oncogenicity is believed to be mediated by DNA recombination with the host cell DNA. The mammalian genome contains certain genes, designated proto-oncogenes, that can acquire oncogenic properties upon transduction into the genome of acute transforming retroviruses (Bishop, Ann. Rev. Biochem. 1983, 52:301; Bishop, Cell 1985, 42:23). In certain human cancers (e.g. T24 and EJ human bladder carcinoma) it has been well documented that the identified transforming gene (H-ras-1 locus) relates to the v-rasH of the Harvey murine sarcoma virus. Among the proto-oncogenes and oncogenes, the ras family has been thoroughly characterized and studied with respect to activation and expression in human neoplasms. When a proto-oncogene undergoes point-mutation (e.g. c-rasH) or rearrangement (e.g. n-myc), such changes can lead to a loss of cell regulation in differentiation and growth, and eventually oncogenesis.

Recently, a transforming DNA sequence from a human (Mahlavu) hepatocellular carcinoma, hhc$^M$ has been identified and molecularly cloned as part of a large fragment (Yang et al, J. Gen. Virol. 1982, 63:25; Yang et al, Environmental Health Perspectives 1985, 62:231). A number of hhc$^M$ related DNA clones from several other human hepatocellular carcinomas have been isolated that exhibited nil to moderate cell transforming activity on NIH/3T3 cells. Two have been partially characterized and they are a moderately cell-transforming gene from Mahlavu hepatocellular carcinoma (hhc$^M$) and a putative cellular homologue (c-hhc) isolated from normal human liver DNA, which has no cell-transforming activity. The biological activities of two molecular clones of hhc$^M$ and a Korean hhc$^{K3}$ and c-hhc have been characterized and compared (Yang et al, Leukemia 1988, 2(12 Supplement):102S). Amplification of the hhc$^M$ sequence in the various genomic DNAs of hepatomas from 2 Chinese, one African and 17 Korean sources, was observed and compared with the distribution of integrated HBV DNA sequences in the same hepatomas in order to provide some insight into the possible role of hhc$^M$.

The present invention relates to an oncoprotein specific for hepatocellular carcinomas and to a nucleotide sequence that codes for such a protein. The invention further relates to diagnostic and screening methodologies (and kits based thereon) that make use of the oncoprotein (or antibodies specific for same) and the nucleotide sequence.

SUMMARY OF THE INVENTION

It is one object of the invention to provide a hepatocellular oncoprotein and a nucleotide sequence coding for same.

It is another object of the invention to provide a diagnostic test for the presence of hepatocellular carcinomas as well as preneoplastic or pathological conditions of the liver.

Further objects and advantages of the present invention will be clear to one skilled in the art from the description that follows.

In one embodiment, the present invention relates to a DNA fragment coding for the amino acid sequence set forth in FIGS. 1A–C or an allelic variation of that sequence, or a unique portion thereof.

In another embodiment, the present invention relates to a recombinant DNA molecule comprising:
  i) a vector, and
  ii) the above-described DNA fragment.

In a further embodiment, the present invention relates to a host cell transformed with the above-described recombinant DNA molecule.

In another embodiment, the present invention relates to a nucleotide fragment sufficiently complementary to the above-described DNA fragment to hybridize therewith.

In a further embodiment, the present invention relates to a protein having the amino acid sequence set forth in FIGS. 1A–C or an allelic variation of that sequence, or a unique portion thereof.

In another embodiment, the present invention relates to antibodies (polyclonal and/or monoclonal) specific for the above-described protein.

In a further embodiment, the present invention relates to a process of producing the above-described protein comprising culturing a host cell transformed with the above-described recombinant DNA molecule under conditions such that the DNA fragment is expressed and the protein thereby produced; and isolating the protein.

In another embodiment, the present invention relates to a method of detecting the presence of the above-described protein in a sample comprising:
  i) contacting the sample with an antibody specific for the protein under conditions such that binding of the antibody to the protein can occur, whereby a complex is formed; and
  ii) assaying for the presence of the complex.

In another embodiment, the present invention relates to a method of detecting the presence of a nucleotide sequence coding for the above-described protein in a sample comprising:
  i) contacting the sample with a nucleotide fragment sufficiently complementary to the nucleotide sequence to hybridize therewith under conditions such that hybridization can occur, whereby a complex is formed, and
  ii) assaying for the presence of the complex.

In a further embodiment, the present invention relates to a method of diagnosing the presence of hepatocellular carcinoma in a patient comprising:
  i) contacting a biological sample from the patient with the above-described antibody under conditions such that binding of the antibody to the protein present in the sample can occur, whereby a complex is formed; and
  ii) assaying for the presence of the complex.

In another embodiment, the present invention relates to a method of diagnosing the presence of hepatocellular carcinoma in a patient comprising:
  i). contacting nucleic acid sequences derived from a cellular sample from the patient with the above-described nucleotide fragment under conditions such that hybridization can occur, whereby a complex is formed; and
  ii) assaying for the presence of the complex.

In another embodiment, the present invention relates to a diagnostic kit for detecting the presence of the above-described protein in a sample comprising a container means having disposed therewithin antibodies specific for the protein.

In a further embodiment, the present invention relates to a diagnostic kit for detecting the presence of a nucleic acid sequence coding for a protein having the amino acid sequence set forth in FIG. 1A–C or an allelic variation of the sequence, or a unique portion thereof, comprising a container means having disposed therewithin the above-described nucleotide fragment.

BRIEF DESCRIPTION OF THE FIGURES

FIG. 1A–C: Complete nucleotide sequence of hhc$^M$ and the amino acid sequence of a 52,000 dalton protein encoded within its open reading frame.

DETAILED DESCRIPTION OF THE INVENTION

Figure 2:
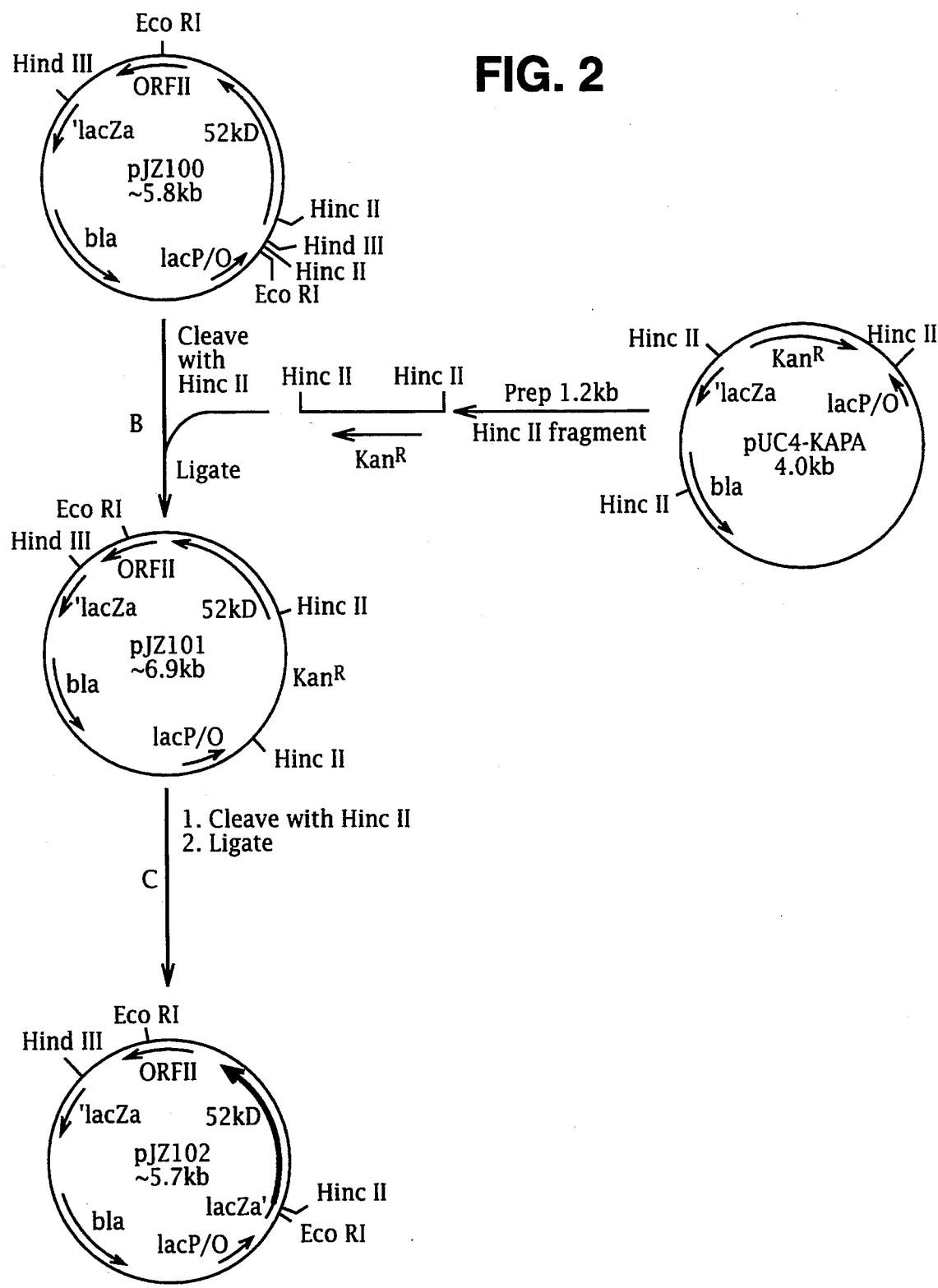
FIG. 2: Construction of hhc$^M$-LacZ chimeric plasmid for the production of the hhc$^M$ 52 kD protein.

The present invention relates to an oncoprotein coded for by a transforming nucleotide sequence of hepatocellular carcinomas and to the transforming sequence itself. The invention further relates to unique portions (i.e., at least 5 amino acids) of the oncoprotein, and to nucleotide sequences (fragments) that code for such polypeptides. The invention further relates to nucleotide segments sufficiently complementary to the above-described nucleotide sequences (fragments) to be used as probes for detecting the presence of such nucleotide sequences (fragments). The invention also relates to diagnostic and screening methodologies for use in detecting the presence of hepatocellular carcinomas (as well as preneoplastic or pathological conditions of the liver) in a warm blood animal.

The oncoprotein of the present invention is an amplified gene expression product of hepatoma cells that is specifically related to hepatomas. The protein can have the complete sequence given in FIG. 1A–C, in which case it is designated hhc$^M$. The protein can also have the amino acid sequence of a molecule having substantially the same properties (e.g., immunological) as the molecule given in FIG. 1A–C (for example, allelic forms of the FIG. 1A–C sequence). Alternatively, the protein (or polypeptide) of the invention can have an amino acid sequence corresponding to a unique portion of the sequence given in FIG. 1 (or allelic form thereof).

The protein can be present in a substantially pure form, that is, in a form substantially free of proteins and nucleic acids with which it is normally associated in the liver. The oncoprotein of the invention, including that made in cell-free extracts using corresponding mRNA, and the oncoprotein made using recombinant techniques, can be purified using protocols known in the art. The oncoprotein, or unique portion thereof, can be used as an antigen, in protocols known in the art, to produce antibodies thereto, both monoclonal and polyclonal.

In another embodiment, the present invention relates, as indicated above, to nucleotide sequences (fragments) (including cDNA sequences) that encode the entire amino acid sequence given in FIG. 1A–C (the specific DNA sequence given in FIG. 1A–C being only one example), or any unique portion thereof. Nucleotide sequences to which the invention relates also include those coding for proteins (or polypeptides) having substantially the same properties (e.g., immunological) of the hhc$^M$ polypeptide (for example, allelic forms of the amino acid sequence of FIG. 1A–C). The invention further relates to nucleotide segments sufficiently complementary to the above-described nucleotide sequences (fragments) to hybridize therewith (e.g. under stringent conditions).

In another embodiment, the present invention relates to a recombinant molecule that includes a vector and a nucleotide sequence (fragment) as described above (advantageously, a DNA sequence coding for the molecule shown in FIG. 1A–C or a molecule having the properties thereof). The vector can take the form of a virus or a plasmid vector. The sequence can be present in the vector operably linked to regulatory elements, including, for example, a promoter (e.g., the e,uns/LacZ/promoter). The recombinant molecule can be suitable for transforming procaryotic or eucaryotic cells, advantageously, protease deficient E. coli cells.

A specific example of a recombinant molecule of the invention is shown in FIG. 2. In this example, the hcc$^M$ nucleotide sequence is placed in a chimeric construct by replacing the codons of the original N-terminus 18 amino acids of the hhc$^M$ p52kD with the procaryote LacZ expression/translation sequence plus codons for 11 amino acids by appropriate recombinant DNA manipulations (Yang et al. Proc. of the XIV Inter. Symp. Sponsored by the International Association for Comparative Research on Leukemia and Related Diseases November 1989 (Vale, Colo.)). Driven by the LacZ promoter, the resultant chimeric gene is expressed at high levels in a protease deficient *E. coli* mutant at 30° C. In a further embodiment, the present invention relates to a host cell transformed with the above-described recombinant molecule. The host can be procaryotic (for example, bacterial (advantageously *E. coli*)), lower eucaryotic (i.e., fungal, including yeast) or higher eucaryotic (i.e. mammalian, including human). Transformation can be effected using methods known in the art. The transformed host cells can be used as a source for the nucleotide sequence described above (which sequence constitutes part of the recombinant molecule). When the recombinant molecule takes the form of an expression system (see specific construct described above), the transformed cells can be used as a source for the oncoprotein.

The oncoprotein and nucleic acid sequence of the present invention can be used both in a research setting (for example, to facilitate an understanding of how and why hepatocellular carcinomas develop) and in a clinical setting to, for example, diagnosis (and/or screening) the presence and/or progress of hepatocellular carcinomas (as well as preneoplastic or pathological condition of the liver).

The diagnostic/screening methodologies referred to above can be carried out using antisera or monoclonal antibodies (produced using known techniques) against the oncoprotein (or unique portions thereof) of the invention. For example, the diagnostic method can take the form of an immunoassay that can be used with urine or serum samples of patients at high risk for hepatocellular carcinoma (e.g. chronic hepatitis carriers) and/or of populations in the geographically identified hot-spots of liver cancer (e.g. Chitung Province of China). The screening immunoassay can be of the simple dip-stick type where binding of one member of the antigen/antibody pair, attached to the stick, with the other member of the pair, present in the sample, is accompanied by a color change (such dip-stick type assays have been described for use with a variety of binding pairs). Such simple tests would be easily and widely applicable to populations in areas where analytical electrophoresis equipment (required for detecting alpha-fetoprotein levels in patients' sera, which levels are currently used in screening and diagnosing the presence of hepatocellular carcinomas) may not be readily available.

The diagnostic methods of the invention can also take the form of histochemical diagnostic tests involving the use of antibodies against the protein or polypeptide of the invention. Such a test can be used on frozen or prefixed liver thin section samples to enable a more definite diagnosis of liver cancer.

The diagnostic methods of the invention can also involve the use of nucleic acid probes sufficiently complementary to a portion of the nucleic acid sequence of the invention to hybridize thereto. Such probes can be used to detect the presence of the endogenous sequence, for example, following electrophoresis of genomic DNA digested with appropriate restriction enzymes. The probe can be labelled, for example, with 32P, to facilitate detection.

The invention further relates to diagnostic/screening kits for use in carrying out the above methods. The kits can comprise, for example, the above-described antibodies specific for the oncoprotein (or polypeptide) of the invention or, alternatively, the above-described nucleic acid probes, together with any ancillary reagents (e.g., buffers, detectable markers, enzyme substrates, etc.) necessary to conducting the test.

The invention is described in further detail in the following non-limiting Examples.

EXAMPLES

The following protocols are referenced in the Examples that follow:
Molecular cloning of hhc$^M$ Genomic DNA purified from human normal liver and Mahlavu (African) hepatocellular carcinoma (HHC), as described below, were subjected to complete digestion by HindIII restriction endonuclease. (Other restriction endonucleases including BamHI, EcoRI and PstI, were also used for isolating genomic DNA fragments from HHC and liver DNA in an attempt to clone HHC DNA sequences; the clones isolated from these efforts were not successful with respect to transfection studies.) The DNA samples both [$^3$H]aflatoxin B$_1$ (AFB$_1$)-epoxide bound (as described below) and unbound, were separated into 180 fractions by polyacrylamide gel electrophoresis. Specificity of [$^3$H]AFB$_1$-epoxide per µg of DNA was determined. Fractions with significant [$^3$H]AFB$_1$-epoxide specific activity were used in DNA transfection assay on NIH3T3 cells as described below. Fractions showing positive focus formation indicating positive cell transformation, were identified and the parallel unbound DNA fractions were molecularly cloned by ligation onto the HindIII site of pBR322, pBR325 and/or Puc 8 plasmid DNAs for transformation of *E. coli* HB101 cells as described elsewhere (Yang et al., J. Gen. Virol. 1982, 63:25). Primary selection of the resultant clones was thus based on (1) the sensitivity to tetracycline, and/or color change associated with the disruption of the lacz operon containing the B-galactosidase coding sequence of the plasmid; and (2) the capability of cell-transformation in transfection assays on NIH3T3 cells with or without AFB$_1$ binding; (3) the presence of human sequence in colony-hybridization and DNA-DNA hybridization against [$^{32}$P]probes prepared from human Alu sequence (Lawn et al., Cell 1978, 15:1157) and also [$^{32}$P] labelled HindIII digested MAH HHC DNA fragments; and (4) [$^3$H]AFB$_1$-epoxide binding on the DNA fragments. After screening over 30,000 clones by these quadruple technical approaches including [$^3$H]AFB$_1$ binding, transfection assay on NIH3T3 cells and DNA-DNA hybridization against the [$^{32}$P]Alu and [$^{32}$P]HindIII MAH HHC DNA probes, three clones were isolated. One particular 3.1 kb DNA restriction fragment constitutes the hhc$^M$ DNA.

Preparation of plasmid DNA and AFB$_1$ binding

The clone used in these studies has been referred to as PM-1. Plasmid DNA was prepared by the Holmes' method, i.e. the rapid heating method, followed by CsCl$_2$-ethidium bromide isopycnic centrifugation at 180,000× g for 20 hrs (Maniatis et al., Molecular Cloning, Cold Spring Harbor Laboratory, Cold Spring Harbor, N.Y. 1982). The banded PM-1 DNA was then purified free of ethidium bromide by isopropanol extraction and exhaustive dialysis against TEN buffer. A yield of 25 to 50 µg of total plasmid DNA per 5 ml of culture was generally obtained. The 3.1 kb hhc$^M$ DNA was then separated from PUC 8 DNA and other contaminants by digesting the PM-1 DNA with HindIII endonuclease and then subjecting to agarose gel electrophoresis and electroelution of the separated 3.1 kb band. The resultant 3.1 kb hhc$^M$ DNA was homogeneously purified and used in AFB$_1$ activation experiments.

The hhc$^M$ 3.1 kb DNA was also cloned into a pSVneo vector that carried a murine retroviral (Moloney) LTR, SV40 promoter and part of the T antigen besides the neomycin resistance gene. This clone, rpMpN-1, is expressed at a significantly higher level when transfected into cells and offers special advantages for transfection assay.

[$^3$H]AFB$_1$ at 15 Ci/mmole specificity was acquired from Morales Laboratory, California. It was further purified by HPLC to homogeneity and the resultant single peak of [$^3$H]AFB$_1$ had the specific activity of 9,250 cpm/pmole. It was used in activation reactions with either mixed function oxidases freshly prepared from liver microsomal preparation or by the chemical peroxidation reaction using perchlorobenzoic acid and methylene chloride as described earlier (Bennett et al., Cancer Res. 1981, 41:650; Garner et al., Chem. Biol. Interact. 1979, 26:57). Binding of [$^3$H]AFB$_1$ epoxide with either high molecular weight HHC or plasmid DNA was monitored by kinetic analysis (Yang et al. Environmental Health Perspective 1985, 62:231 and Modali and Yang, Monitoring of Occupational Genotoxicants pp. 147–158 (1986)). Sample withdrawn at each time point was washed free of unbound [$^3$H]AFB$_1$ epoxide with chloroform, and ethanol precipitated prior to redissolving the [$^3$H]AFB$_1$-DNA in Tris-EDTA-NaCl (TEN) buffer for transfection assay or sequence analysis.

Cells, tissue culture and transfection assay

NIH/3T3 cells, passage 6 to 11, and Buffalo rat liver cells (BRL-1) for transfection assays, were maintained in Dulbecco's modified Eagle's media supplemented with 10% heat-inactivated fetal calf serum, penicillin (50 units ml$^{-1}$) and streptomycin (25 μg ml$^{-1}$) (DMEM) in a 5% CO$_2$ atmosphere, at 37° C.

DNA transfection was carried out as described earlier (see Yang et al. 1985 and Modali and Yang 1986, referenced above). Optimal conditions were achieved by carefully titrating the pH curve for the DNA-calcium phosphate complex mixture; it was usually found that pH 6.75 ensured a fine complex precipitation.

Preparations of DNA and RNA from tissue culture cells and tumor tissues

Total high molecular weight (HMW) DNA was extracted and purified from tissue culture cells and tumor tissues as described elsewhere (Yang et al., 1985 referenced above). The HMW DNA thus purified, has been subjected to proteinase K digestion, first sequential chemical purification with phenol-cresol, chloroform-isoamyl alcohol, ether and ethanol-NaCl precipitation, followed by RNase digestion and a second sequential chemical purification. The purified DNAs were then dialyzed against TEN buffer for use in experiments. Total RNA was extracted from tissue culture cells and prepared as described previously (Maniatis et al., 1982 referenced above). Poly A rich RNA was obtained by affinity separation with oligo dT cellulose (Collaborative Research, Massachusetts) column elution.

Tumorigenesis

Transformed cells, cloned out from the transfected cell culture by either cloning cylinder method or terminal dilution method, were expanded and inoculated at 10$^4$ to 10$^6$ cells into athymic Swiss nu/nu mice subcutaneously. Tumorigenesis in the challenged mice was monitored closely.

Nucleotide sequence analysis and site-targeted mutagenesis

Nucleotide sequencing of the hhc$^M$ 3.1 kb and variants produced by site-targeted mutagenesis were carried out by the standard Maxam-Gilbert Methods in Enzymology 1980, 65:499 and the Sanger (M13) dideoxy sequencing methods (Maniatis et al., 1982 referenced above).

Specified oligonucleotide sequence of 20 mers carrying the targeted dG→T mutation were synthesized by the Applied Biosystem oligonucleotide synthesizers. They were used as templates in generating the mutated clones. Mutant DNA clones were produced in accordance with the protocol provided by and using the oligonucleotide-directed in vitro system of Amersham (Arlington Hts., Ill.). DNAs of the mutated clones were verified by nucleotide sequencing. Effects of these site-targeted mutagenized DNA were analyzed by potentiation of cell-transformation in transfection assay on NIH/3T3 cells and RNA expressions in transfected cells using the BRL dot-blot technique (Bethesda Research Laboratory, Rockville, Md.).

EXAMPLE I

Figure 3:
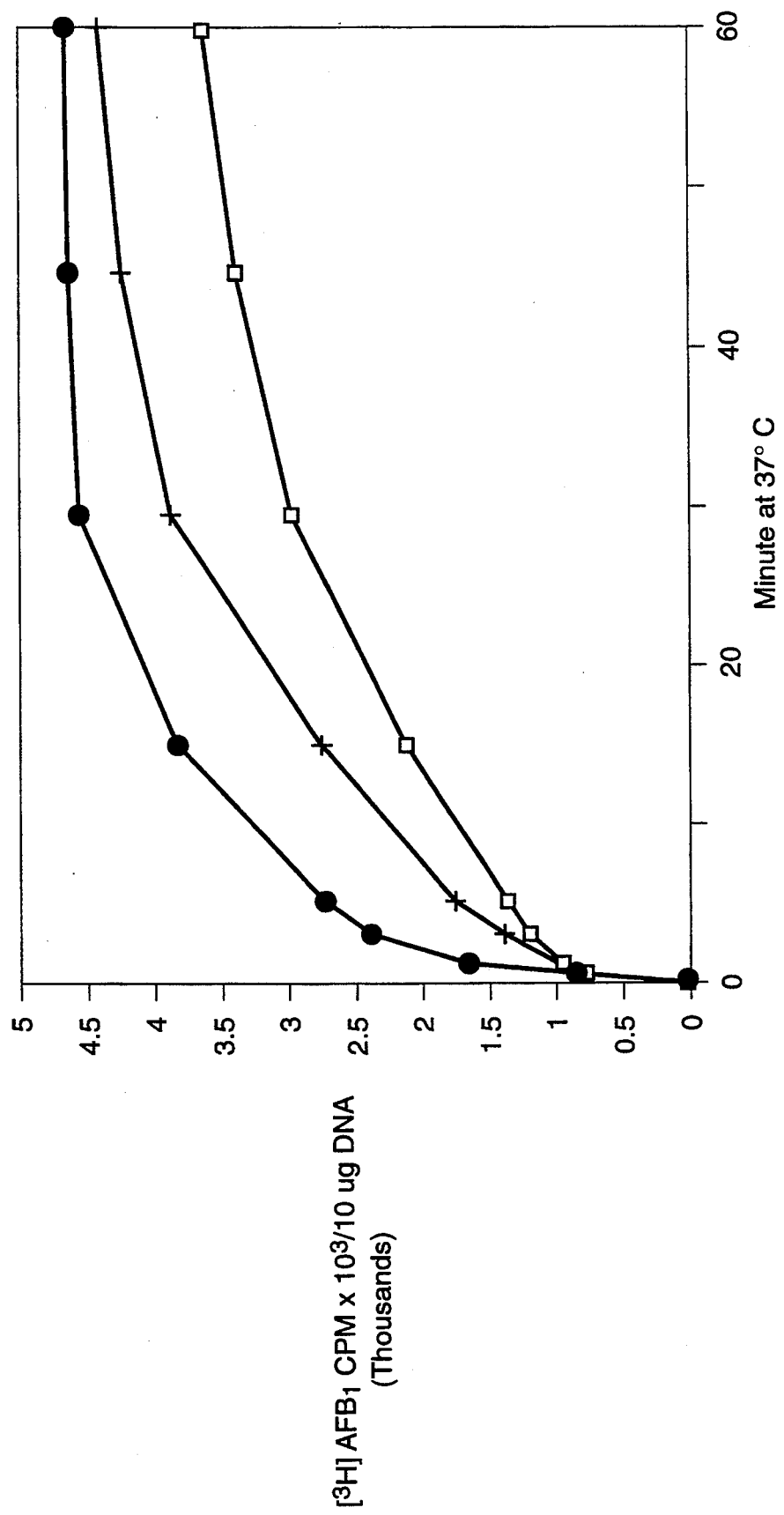
FIG. 3: Aflatoxin B$_1$ epoxide binding on high molecular weight DNAs prepared from human hepatocellular carcinoma (Mahlavu), human normal liver and from murine (NIH/3T3) fibroblasts.

Dosimetry of AFB$_1$ binding and potentiation of hhc$^M$ cell-transformation capability on NIH/3T3 cells AFB$_1$ epoxide binds high molecular weight DNAs prepared from human hepatoma, human liver and mouse NIH/3T3 cells efficiently (FIG. 3). The initial rates in each binding kinetic were extremely rapid. The rates of AFB$_1$-epoxide binding to human normal liver or hepatoma DNA and to murine NIH/3T3 cell DNA became significantly different after one minute of binding reaction. The MAH HHC DNA showed a greater rate of binding than normal liver DNA and all the dG targets became saturated earlier, whereas AFB$_1$ epoxide bound the normal liver DNA at a slower rate but eventually saturated all the dG targets at a slightly lower level. The human DNAs showed a higher level of AFB$_1$ binding than the murine NIH/3T3 cell DNA. The overall AFB$_1$ specific activity, i.e. AFB$_1$-dG adduct, was found to be about one dG bound per 10 nucleotides among these high molecular weight double stranded DNAs. This overall specificity also took into consideration the existence of secondary or tertiary structure of the high molecular weight DNAs. AFB$_1$ epoxide binding on linearized 3.1 kb double stranded hhc$^1$DNA was consistently found to be 4 to 8 dG bound per 10$^4$ nucleotides. This higher binding capability reflects the relatively easy accessibility of dG within the linearized double stranded PM-1 DNA by AFB$_1$ epoxide and should not be compared with the efficiency of AFB$_1$-dG adduct formation with high molecular weight native double-stranded DNA.

Within a finite dosimetry the binding of AFB$_1$ epoxide with dG potentiates the cell-transformation capability of hhc$^M$ by 10 to 20 fold as seen in the experiment illustrated in Table 1.

TABLE 1

| AFB$_1$ Dose-dependent Activation of PM-1 DNA in The transformation of NUH/3T3 cells | | |
|---|---|---|
| DNA Source | AFB$_1$ femtomole per 100 ng DNA | Number of Foci per 100 ng DNA |
| hhc$^M$ (PM-1) | 0 | 15 × 10$^{-1}$ |
| c-Ha-ras-1 | 0 | 465 |
| c-K-ras-1 | 0 | 0 |

TABLE 1-continued

AFB$_1$ Dose-dependent Activation of PM-1 DNA in The transformation of NUH/3T3 cells

| DNA Source | AFB$_1$ femtomole per 100 ng DNA | Number of Foci per 100 ng DNA |
|---|---|---|
| c-hhc (human liver homolog) | 0 | 0 |
| E. coli | 0 | 0 |
| hhc$^M$ (PM-1) | 0 | 15 × 10$^{-1}$ |
| hhc$^M$ (PM-1) | 5 | 18 |
|  | 14 | 26 |
|  | 24 | 66 |
|  | 35 | 3 |
| c-hhc | 0 | 0 |
|  | 8 | 0 |
|  | 15 | 0 |
|  | 30 | 0 |
|  | 40 | 0 |

AFB$_1$ binding and transfection assay were as described in Methods. Data were calculated on the basis of per 100 ng. In the assay with unbound hhc$^M$ DNA the transfection assays were carried out with 500 ng to 1.5 ug of DNA in order to obtain reasonable foci formation on NIH/3T3 cells. Transfection with AFB$_1$-epoxide bound DNA was carried out at a range of 50 to 500 ng DNA.

Data were normalized to show potentiation of hhc$^M$ cell-transformation capability by AFB$_1$-epoxide activation.

Whereas the efficiency of unbound PM-1 DNA in transforming NIH/3T3 cells was usually observed at about 15 FFU/ μg DNA the efficiency of AFB$_1$ epoxide activated PM-1 DNA was optimized at 66 FFU/100 ng DNA, an increase of 20 fold. The possibility of non-specific mutagenization accounting for this potentiation were considered. That this potentiation effect was due to free AFB$_1$ that diffused into the cell or recycling of AFB$_1$ adducts has been ruled out earlier with the appropriate control experiments which showed that activation of normal liver or E. coli DNA at the same dosimetry failed to activate any cell-transforming capability (Yang et al., 1985 referenced above). Moreover in this experiment with AFB$_1$ activated DNA from c-ras$^k$-1 or c-hhc, a normal human liver homolog to hhc$^M$ as the appropriate controls, no cell-transformation of NIH/3T3 cells was obtained suggesting that AFB$_1$ epoxide activated PM-1 DNA was not a random phenomenon. Moreover the AFB$_1$ dose-dependency of PM-1 DNA in cell-transformation efficiency (Table 1) further substantiated the specificity of AFB$_1$ epoxide binding in conferring the potentiation of cell-transformation. Whereas optimal dosimetry was seen at 24 femtomole AFB$_1$/100 ng of PM-1 DNA, at dosimetry beyond 45 femtomole per 100 ng of PM-1 DNA, an over-kill effect was observed. No transformed foci were obtained in NIH/3T3 cells transfected with AFB$_1$ epoxide bound PM-1 DNA although human DNA was incorporated into the NIH/3T3 cells in a degraded form (Yang et al., 1985 and Modali and Yang, 1986 referenced above). This observation suggested that over activation of PM-1 DNA not only generated scissions in the molecule but possibly degradation leading to a loss of biological activity. It was also evident from these results that no more than one or at most a few AFB$_1$-dG adducts per PM-1 DNA molecule could be tolerated by the hhc$^M$ DNA before the biological activity of the hhc$^M$ DNA became compromised and at the risk of survival. Moreover the potentiation of hhc$^M$ DNA in cell-transformation probably necessitates no more than one or at most a finite number of AFB$_1$ bindings.

EXAMPLE II

Specificity of the AFB$_1$-epoxide binding on dG's of PM-1 DNA

Figure 4:
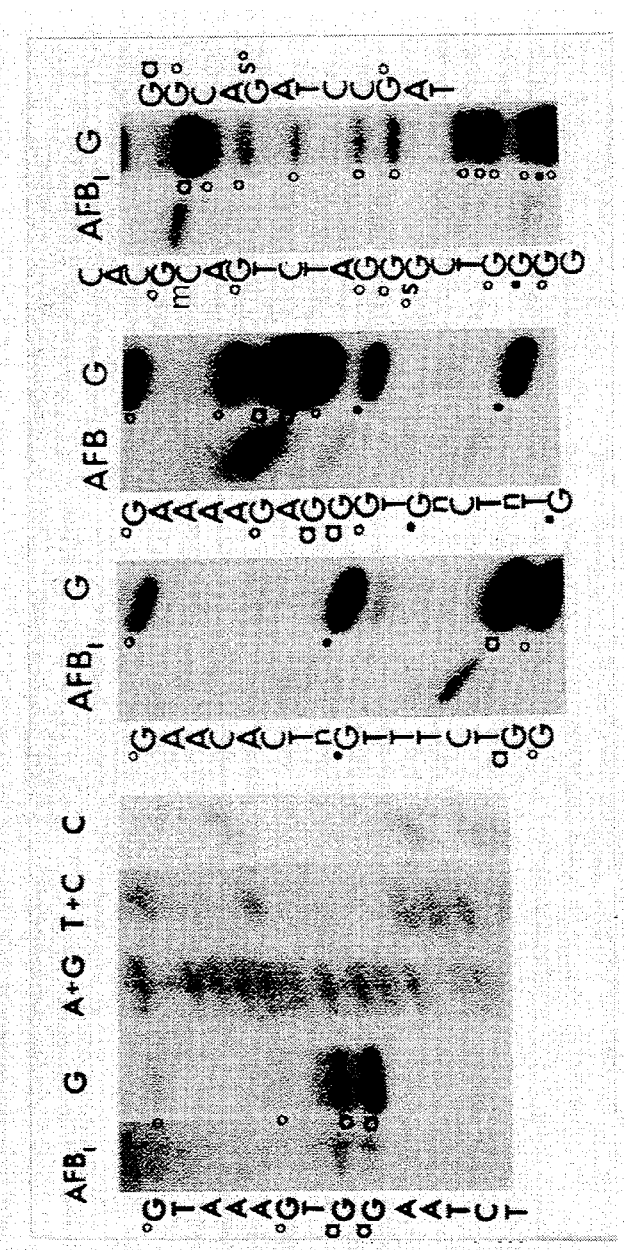
FIG. 4: Identification of the dG bound by AFB$_1$ epoxide within the hhc$^M$ (PM-1) DNA by a modified Maxam-Gilbert sequencing method. Nucleotide sequences are specified on the side. The left panel illustrates ladder for all four deoxynucleotides and AFB$_1$-dG; only native dG and AFB$_1$-dG were given in all other three panels on the right. aG=AFB$_1$ bound dG at all time; °G=dG that was not reacted with AFB$_1$; whereas °G=moderately preferred dG.

Deoxyguanine nucleotide of native DNA, when bound by AFB$_1$ epoxide, became alkali and therefore could be identified by piperidine cleavage; whereas unbound deoxyguanine nucleotide within the same native DNA would not cleave without dimethyl sulfide (alkali) treatment. FIG. 4 shows the dG targets within the PM-1 DNA when bound at a saturation conditions. When the targeted sequences are evaluated in sets of tetranucleotides, an empirical formulation can be derived on the basis of the binding pattern of AFB$_1$ epoxide with the dG's in PM-1 DNA. Table 2 summarizes the nucleotide sequence in a set of tetranucleotides that were seen and targeted by AFB$_1$ epoxide. As shown in FIG. 4, the dG within a sequence of any one of the following tetranucleotides of AGAG, AGTT, TGTT, TGAT, or AGAA, escaped attack by AFB$_1$ epoxide and hence showed no cleavage in the sequence without prior DMS treatment. This is confirmed by the distinct cleavage of dG as a result of AFB$_1$ epoxide attack on dG in sequences of GGGC, CGGC, AGGC, TGGC or CGCG. Upon evaluating the various sequences in which a dG target could be accessed by AFB$_1$ epoxide, it can be concluded that within a double stranded DNA, the least likely dG target would be that flanked by dA and dT, i.e. category III. The most likely dG target would be that flanked by dG and/or dC, i.e. category I, and that tetranucleotide sequences in which dG is either preceded by dA or T and followed by dG and dC would be the moderately preferred targets of AFB$_1$ epoxide, i.e. category II. This, of course, does not take into consideration the secondary or the tertiary structure of the DNA in its natural state since these analyses were done on linearized double-stranded DNA. It should also he mentioned that whereas the dG binding affinity of AFB$_1$-epoxide was greatly affected by the vicinal nucleotides in the double-stranded PM-1 DNA, no specificity was observed with respect to AFB$_1$-epoxide binding to dG in single stranded DNA. The observations of Modali and Yang (1986 referenced above) were basically in agreement with others working on AFB$_1$ binding on OX174 and pBR 322 DNAs (Misra et al., Biochemistry, 1983, 22:3351).

TABLE 2

Vicinal Nucleotide Sequence Dictates The dG Targets of AFB$_1$-Epoxide Binding*

| Preferred Targets Category I | Least Favored Targets Category III |
|---|---|
| * | * |
| GGGG | AGAG |
| GGGC | AGTG |
| GGGA | AGAA |
| GGGT | AGAC |
|  | AGAT |
| CGGG | TGAG |
| AGGG | TGAC |
| TGGG | TGAA |
|  | TGAC |
| CGGC | TGTG |
| AGGC | TGTA |
| TGGC | TGTC |
|  | TGTT |
| CGGA |  |
| AGGA |  |
| TGGA |  |
| CGGT |  |
| AGGT |  |

TABLE 2-continued

Vicinal Nucleotide Sequence Dictates The dG Targets of AFB₁-Epoxide Binding*

| Preferred Targets Category I | Least Favored Targets Category III |
|---|---|
| | TGGT |

*This table represents the dG targets of AFB$_1$-epoxide binding observed in studies with linearized double stranded PM-1 DNA. Moderately preferred dG targets, i.e. Category II, are omitted here but are described elsewhere (Modali and Yang, 1986).

Within the past two years, the nucleotide sequence of hhc$^M$ has been resolved by a combination of Maxam-Gilbert nucleotide sequencing technique and the M13 dideoxy method using the BRL kilobase sequencing system. Applying these empirical rules in computer analysis of the hhc$^M$ 3.1 kb nucleotide sequence, the most and moderately preferred dG targets within the various loci of hhc$^M$ have been predicted (Table 3). Although a maximum number of 60 dG targets was predicted on the basis of AFB$_1$-epoxide binding studies with linearized 3.1 kb hhc$^M$ DNA, it was evident upon examining the possible secondary and tertiary structure of hhc$^M$ sequence, that a much lower number of dG targets would be accessible by AFB$_1$-epoxide. Moreover, only a few such induced mutations would produce any effect of survival value.

TABLE 3

Predicted dG Targets within The Nucleotide Sequence of hhc$^M$ Preferrentailly Attacked by AFB$_1$-Epoxide

| *CGCC | *CGGC *CGGC | *GGCC | *GGGC | *GGGA *GGGA | *AGGA *AGGA | *TGCC | *TGCG | *TGGA *TGGA | *TGGG *TGGG | *GGAG |
|---|---|---|---|---|---|---|---|---|---|---|
| | | | | 73 | | | | | | |
| | | | | 74 | | | | | | |
| | | | | | 84 | | | | | |
| | | | | | | | | 97 | | |
| | | | | | | | | 98 | | |
| | | | 125 | | | | | | | |
| | | | 126 | | | | | | | |
| | | | | | | | | | 140 | |
| | | | | | | | | 221 | | |
| | | | | 223 | | | | | | |
| | | | | 224 | | | | | | |
| | | | | 307 | | | | | | |
| | | | | 308 | | | | | | |
| | | | | | | | | 371 | | |
| | | | | | | | | 391 | | |
| | | 472 | | | | | | | | |
| | | | | | | | | | 481 | |
| | | | | | | | | | 492 | |
| | | | 494 | | | | | | | |
| | | | 495 | | | | | | | |
| | | | | | 539 | | | | | |
| | | | | | | | | | | 550 |
| | | | 560 | | | | | | | |
| | | | 561 | | | | | | | |
| | | 577 | | | | | | | | |
| | | | 692 | | | | | | | |
| | | | | | | | | | 860 | |
| | | | | | 901 | | | | | |
| | | | | | 1125 | | | | | |
| | | | 1320 | | | | | | | |
| | | | 1321 | | | | | | | |
| | | | | | | | | 1330 | | |
| | | | | | | | | | 1354 | |
| | | | | | | | | | 1404 | |
| | 1405 | | | | | | | | | |
| | | | 1431 | | | | | | | |
| | 1543 | | | | | | | | | |
| | 1588 | | | | | | | | | |
| | | | | | | | | | 1637 | |
| | | | | | | | | 1652 | | |
| | | | 1765 | | | | | | | |
| | | | | | | | 1815 | | | |
| | 1853 | | | | | | | | | |
| | | | | | | | 1862 | | | |
| | | | | | | | | | | 1868 |
| | | | | | | | | 1878 | | |
| | | | | | | | 1986 | | | |
| | | | 2064 | | | | | | | |
| | | | | | | | 2094 | | | |
| | 2205 | | | | | | | | | |
| | | | | | | | | | 2315 | |
| | | | | | | | | | 2331 | |
| | | | 2352 | | | | | | | |
| | | | 2352 | | | | | | | |
| | | | | | | | | | 2460 | |
| 2482 | | | | | | | | | | |
| | | | | | | | | | 2718 | |
| | | | | | | | | 2797 | | |
| | | | | | | | | | 2884 | |

TABLE 3-continued
Predicted dG Targets within The Nucleotide Sequence of hhc$^M$ Preferrentailly Attacked by AFB$_1$-Epoxide

| * | * | * | * | * | * | * | * | * | * | * |
|---|---|---|---|---|---|---|---|---|---|---|
| CGCC | CGGC | GGCC | GGGC | GGGA | AGGA | TGCC | TGCG | TGGA | TGGG | GGAG |
|  | * |  |  | * | * |  |  | * | * |  |
|  | CGGC |  |  | GGGA | AGGA |  |  | TGGA | TGGG |  |

2926

In order to analyze the possible effect of any such AFB$_1$ induced dG→T mutation, site-targeted mutagenesis study of the hhc$^M$ DNA was initiated using polynucleotides of 20 mers that carried a predicted dG→dT point-mutation, presumably the result of an AFB$_1$-epoxide mutagenesis. Thus far, only a few of the predicted dG→dT mutagenesis sites have been analyzed and these are summarized in Table 4. The recombinant construct carrying the hhc$^M$ sequence in the SV40 T antigen vector plus a neomycin resistance marker, rpN$^r$pM-1 was used in this study since it offered the advantage of selecting the transfected cells by its resistance to Gentamicin sulfate (G418), an analog of neomycin. Using expression of hhc$^M$ specific mRNA as a criterion, we analyzed by Northern dot-blot in a semi-quantitative assay of the mRNA, i.e. poly A enriched RNA, expressed in the G418 resistant NIH/3T3 cells after transfection with the mutagenized hhc$^M$ sequence. Focal transformation in these cells was monitored for 4 to 6 weeks.

Results from seven mutagenized clones, for which nucleotide sequence confirmation was available, suggested that, thus far, mutation leading to a structural protein alteration did not seem to potentiate the cell-transformation of hhc$^M$ (Table 4). Alternatively the introduced dG→T mutations which led to amino acid substitution, thus far, have not altered cell-transformation or expression of mRNA levels. These included mutation at 577 which caused an amino acid substitution of Gly→Val, and mutation at 1005 which resulted in no amino acid substitution because of the wobbling code.

Within the hhc$^M$ nucleotide sequence, there exists an apparent open reading frame, ORF, coding for a polypeptide of about 467 amino acids. This was in good agreement with a 55-57 kD protein and some smaller polypeptide including one 53 kD protein observed in cell-free protein synthesis using hhc$^M$-specific. mRNA in a rabbit reticulocyte lysate system. dG→T mutations at nucleotide 73 and 74 in the 5' terminus, which bears the consensus sequence for ribosomal RNA binding site just 5' ahead of the first methionine codon, blocked cell transformation although hhc$^M$ specific mRNA level showed no difference. This could be the result of blocking protein synthesis. Likewise, interpreted as mutations at 492 and 550 also blocked cell-transformation since a stop codon (UGA) was introduced in each case to stop protein synthesis prematurely.

It was of interest to note that dG→T mutation at 626 generated a sequence resembling the enhancer sequence for RNA polymerase II, which was reported to function even within the coding sequence (footnote of Table 4). The level of mRNA level was increased by 1.5 fold and cell transformation seemed to be enhanced by a slight increase in the number of foci per μg of DNA. This observation suggested that one possible action by which AFB$_1$ induced mutation in hhc$^M$ which itself is a moderately transforming DNA sequence, led to increase in its transformation potential is through augmentation of hhc$^M$ expression. This is analogous to other observations which also indicated that an elevated expression of the cellular ras proto-onocgene driven by a murine LTR sequence, containing both promoter and enhancer sequence, also led to cell transformation in tissue culture cells predisposed to immortality.

TABLE 4
The Effect of dG – – > dT Mutation Induced by Site-Targetted Mutagenesis Within The hhc$^M$ DNA Sequence

| # on hhc$^M$ | Sequence | mRNA Synthesis# | Cell Transformation# |
|---|---|---|---|
| 73 | * AGGA – – > ATGA | + | –@1 |
| 74 | * AGGA – – > AGTG | + | –@1 |
| 492 | * TGGG – – > TGTG | + | –@2 |
| 550 | * GGAG – – > GTAG | + | –@2 |
| 577 | * GGGC – – > GTGC | + | + |
| 626 | * GGGG – – > GTGG | ++ | ++@3 |
| 1005 | * TGCA – – > TTCA | + | + |

@1 Disruption of ribosomal RNA (16S) binding site: AGGA.
                                                       *
@2 Creation of a stop codon: UGA.
                            *
@3 Creation of an enhancer sequence: GGTGTGGTAAAG (Watson et al., 1987; Dynan and Tjian, 1985; Schaffner et al. 1985) and hence increases expression.
Cell transformation was determined by transfection analysis as described in Methods and mRNA synthesis in transfected cells was determined by Northern dot-blot analysis with [$^{32}$P]3.1 kb hhc$^M$ DNA.

The entire contents of all references cited herein are hereby incorporated by reference.

The present invention has been described in some detail for purposes of clarity and understanding. One skilled in the art will appreciate from a reading of this disclosure that various changes in form and detail can be made without departing from the true scope of the invention.

What is claimed is:

1. An isolated DNA fragment consisting of a nucleotide sequence coding for the amino acid sequence set forth as follows

```
81
ATG  TTG  CCC  TTC  ACT  TGT  GGA  AGA  AAT
MET  Leu  Pro  Phe  Thr  Cys  Gly  Arg  Asn

108
GCA  AAT  GAA  AAC  AGC  CCT  AGG  GAT  GTT
Ala  Asn  Glu  Asn  Ser  Pro  Arg  Asp  Val

135
GAC  GTT  GGG  GTG  GCA  CCT  GCT  GCA  GAG
Asp  Val  Gly  Val  Ala  Pro  Ala  Ala  Glu

162
GGT  AAC  GTG  CAG  CAT  GTC  GAG  GGC  AGC
Gly  Asn  Val  Gln  His  Val  Glu  Gly  Ser
```

```
189
ACT GCC AAG GCT GGT TTG AGC TCA AGG
Thr Ala Lys Ala Gly Leu Ser Ser Arg

216
TCA GGT GGA GGA GGT AGT CTC TCC CAT
Ser Gly Gly Gly Gly Ser Leu Ser His

243
CTC TTC TGC GAG TGC AGC TCT AAA CCC
Leu Phe Cys Glu Cys Ser Ser Lys Pro

270
TGC CTG AAA CAC GTG GAG AAG CTA TCT
Cys Leu Lys His Val Glu Lys Leu Ser

297
GAG CTG CCT CCA GGA CAC ATG CAA ATG
Glu Leu Pro Pro Gly His MET Gln MET

324
GAC ACT CTG ATC ATA AAA TTA TCA GGA
Asp Thr Leu Ile Ile Lys Leu Ser Gly

351
AGA TTG AGA AAT AAG ACA AAA ATG GAG
Arg Leu Arg Asn Lys Thr Lys MET Glu

378
GTG CCA CCA AAC CAG TGG AAA TTT TTC
Val Pro Pro Asn Gln Trp Lys Phe Phe

405
CCC TTT TCA TTC CTC TGG CAT TCC CTG
Pro Phe Ser Phe Leu Trp His Ser Leu

432
GCC TTG ACT CAA GGC AGC CCA CAC TCT
Ala Leu Thr Gln Gly Ser Pro His Ser

459
AGG AGC AGA CAC CAG GGC ACA GGT GGG
Arg Ser Arg His Gln Gly Thr Gly Gly

486
GAG CTC TGG GGG ACC CTC CAG GCT TAC
Glu Leu Trp Gly Thr Leu Gln Ala Tyr

513
TCA GTG AAT GGG TTA GCA GCA GCC ACA
Ser Val Asn Gly Leu Ala Ala Ala Thr

540
GGA GCC ACC ATG GAG CCT GCA GGG ACC
Gly Ala Thr MET Glu Pro Ala Gly Thr

567
CAC AAC ACT GAG GGC AGG GAT CTT GCC
His Asn Thr Glu Gly Arg Asp Leu Ala

594
TCT AAT CAG ATA AGC TGT GAT TCC CGA
Ser Asn Gln Ile Ser Cys Asp Ser Arg

621
GAG GGT GGG GTA AAG GCC ACG GGT CTT
Glu Gly Gly Val Lys Ala Thr Gly Leu

648
TTT CTC TCC ACA TCT TCC CAC GTC ATG
Phe Leu Ser Thr Ser Ser His Val MET

675
ACC CCA GAG GGT CGA AGA GGG AGA AAG
Thr Pro Glu Gly Arg Arg Gly Arg Lys

702
TGT GAG CAC CGT GAC ATA ATG AGC CGC
Cys Glu His Arg Asp Ile MET Ser Arg

729
AGC CTT CTG ACT AGA TGC CCC AAA GAA
Ser Leu Leu Thr Arg Cys Pro Lys Glu

756
GAA TCC CAG GTG ACC ACA CAG CAT CAG
Glu Ser Gln Val Thr Thr Gln His Gln

783
AGA AAC TGC AGG GTA ATG AGG AAC TTT
Arg Asn Cys Arg Val MET Arg Asn Phe

810
GGA AAG CAA TCC ATC GTG TTG TCA GTA
Gly Lys Gln Ser Ile Val Leu Ser Val

837
AAA CCT CTG GCT CAC TCC CGA GCT GGG
Lys Pro Leu Ala His Ser Arg Ala Gly

864
CAT GCA TGG ATG GTG ACC CTC GAT GGA
His Ala Trp MET Val Thr Leu Asp Gly

891
ATA GAC TAT GAG GAA CCA GGT GAG GGG
Ile Asp Tyr Glu Glu Pro Gly Glu Gly

918
ATC TAC CTC CAC CGA GAC GTG AGA GTG
Ile Tyr Leu His Arg Asp Val Arg Val

947
ACC TGC ATA CCC AAA CAC CAT GAG GCT
Thr Cys Ile Pro Lys His His Glu Ala

974
TTA AAG ACT GAG CTG ATG TGG AAG CCA
Leu Lys Thr Glu Leu MET Trp Lys Pro

999
CAG CCT CTG CAG GTT GCT CTG CAC TTG
Gln Pro Leu Gln Val Ala Leu His Leu

1028
CAA CAT AAG CCC AAC CAC ATC AAT TGC
Gln His Lys Pro Asn His Ile Asn Cys

1053
TGC AAA ACA AAA CTA CAG CAT TCT CCA
Cys Lys Thr Lys Leu Gln His Ser Pro

1080
TAC CAC TTA AAT AAG ACA CAG AGT CTC
Tyr His Leu Asn Lys Thr Gln Ser Leu

1107
ACA ACA TTC AAA ACG CCC AGG ACA CAA
Thr Thr Phe Lys Thr Pro Arg Thr Gln

1134
TCC AAA ATT ACT TCT ACA AAA AAT CAG
Ser Lys Ile Thr Ser Thr Lys Asn Gln

1161
GAA AAT CTC AAT GAG CAA GGA AAA TGG
Glu Asn Leu Asn Glu Gln Gly Lys Trp

1188
CAA TCA GTA GCT GCC AGT GCT GAG ATG
Gln Ser Val Ala Ala Ser Ala Glu MET

1215
ACA ATG AGG GTT GGA ATC ATC AAC ATC
Thr MET Arg Val Gly Ile Ile Asn Ile

1248
TTT AAA GTA ATT ATC ATA AGC ATT CTC
Phe Lys Val Ile Ile Ile Ser Ile Leu
```

```
1270
CAG CAA GTA ATG GCA AAC ACT CTT GAG
Glu Gln Val MET Ala Asn Thr Leu Glu

1296
ATA AAT GGA AAG ATA AGA AGG CTC AGG
Ile Asn Gly Lys Ile Arg Arg Leu Arg

1323
GAG AAA GTG GAA TGT ACA AAG AAT GAC
Glu Lys Val Glu Cys Thr Lys Asn Asp

1350
CAA GTG GGA ATT GCA CCA CTG GAA ACA
Gln Val Gly Ile Ala Pro Leu Glu Thr

1377
AAT CAC CAG GAT AAA GCA GTC TCT GGC
Asn His Gln Asp Lys Ala Val Ser Gly

1404
TGG GCC AAC AGG AGA ATG GAA ATG AAA
Trp Ala Asn Arg Arg MET Glu MET Lys

1431
AGG GAA AGA GTT GTT ATG GCA GTT GTC
Arg Glu Arg Val Val MET Ala Val Val

1458
CAA TTT GAA CAA CAC AAA AGA CAC
Gln Phe Glu Gln His Lys Arg His .
```

2. The DNA fragment according to claim 1 consisting of nucleotide sequence as follows and wherein said fragment codes for the amino acid sequence set forth as follows

```
81
ATG TTG CCC TTC ACT TGT GGA AGA AAT
MET Leu Pro Phe Thr Cys Gly Arg Asn

108
GCA AAT GAA AAC AGC CCT AGG GAT GTT
Ala Asn Glu Asn Ser Pro Arg Asp Val

135
GAC GTT GGG GTG GCA CCT GCT GCA GAG
Asp Val Gly Val Ala Pro Ala Ala Glu

162
GGT AAC GTG CAG CAT GTC GAG GGC AGC
Gly Asn Val Gln His Val Glu Gly Ser

189
ACT GCC AAG GCT GGT TTG AGC TCA AGG
Thr Ala Lys Ala Gly Leu Ser Ser Arg

216
TCA GGT GGA GGA GGT AGT CTC TCC CAT
Ser Gly Gly Gly Gly Ser Leu Ser His

243
CTC TTC TGC GAG TGC AGC TCT AAA CCC
Leu Phe Cys Glu Cys Ser Ser Lys Pro

270
TGC CTG AAA CAC GTG GAG AAG CTA TCT
Cys Leu Lys His Val Glu Lys Leu Ser

297
GAG CTG CCT CCA GGA CAC ATG CAA ATG
Glu Leu Pro Pro Gly His MET Gln MET

324
GAC ACT CTG ATC ATA AAA TTA TCA GGA
Asp Thr Leu Ile Ile Lys Leu Ser Gly

351
AGA TTG AGA AAT AAG ACA AAA ATG GAG
Arg Leu Arg Asn Lys Thr Lys MET Glu

378
GTG CCA CCA AAC CAG TGG AAA TTT TTC
Val Pro Pro Asn Gln Trp Lys Phe Phe

405
CCC TTT TCA TTC CTC TGG CAT TCC CTG
Pro Phe Ser Phe Leu Trp His Ser Leu

432
GCC TTG ACT CAA GGC AGC CCA CAC TCT
Ala Leu Thr Gln Gly Ser Pro His Ser

459
AGG AGC AGA CAC CAG GGC ACA GGT GGG
Arg Ser Arg His Gln Gly Thr Gly Gly

486
GAG CTC TGG GGG ACC CTC CAG GCT TAC
Glu Leu Trp Gly Thr Leu Gln Ala Tyr

513
TCA GTG AAT GGG TTA GCA GCA GCC ACA
Ser Val Asn Gly Leu Ala Ala Ala Thr

540
GGA GCC ACC ATG GAG CCT GCA GGG ACC
Gly Ala Thr MET Glu Pro Ala Gly Thr

567
CAC AAC ACT GAG GGC AGG GAT CTT GCC
His Asn Thr Glu Gly Arg Asp Leu Ala

594
TCT AAT CAG ATA AGC TGT GAT TCC CGA
Ser Asn Gln Ile Ser Cys Asp Ser Arg

621
GAG GGT GGG GTA AAG GCC ACG GGT CTT
Glu Gly Gly Val Lys Ala Thr Gly Leu

648
TTT CTC TCC ACA TCT TCC CAC GTC ATG
Phe Leu Ser Thr Ser Ser His Val MET

675
ACC CCA GAG GGT CGA AGA GGG AGA AAG
Thr Pro Glu Gly Arg Arg Gly Arg Lys

702
TGT GAG CAC CGT GAC ATA ATG AGC CGC
Cys Glu His Arg Asp Ile MET Ser Arg

729
AGC CTT CTG ACT AGA TGC CCC AAA GAA
Ser Leu Leu Thr Arg Cys Pro Lys Glu

756
GAA TCC CAG GTG ACC ACA CAG CAT CAG
Glu Ser Gln Val Thr Thr Gln His Gln

783
AGA AAC TGC AGG GTA ATG AGG AAC TTT
Arg Asn Cys Arg Val MET Arg Asn Phe

810
GGA AAG CAA TCC ATC GTG TTG TCA GTA
Gly Lys Gln Ser Ile Val Leu Ser Val

837
AAA CCT CTG GCT CAC TCC CGA GCT GGG
Lys Pro Leu Ala His Ser Arg Ala Gly

864
CAT GCA TGG ATG GTG ACC CTC GAT GGA
His Ala Trp MET Val Thr Leu Asp Gly

891
ATA GAC TAT GAG GAA CCA GGT GAG GGG
Ile Asp Tyr Glu Glu Pro Gly Glu Gly
```

918
ATC TAC CTC CAC CGA GAC GTG AGA GTG
Ile Tyr Leu His Arg Asp Val Arg Val

947
ACC TGC ATA CCC AAA CAC CAT GAG GCT
Thr Cys Ile Pro Lys His His Glu Ala

974
TTA AAG ACT GAG CTG ATG TGG AAG CCA
Leu Lys Thr Glu Leu MET Trp Lys Pro

999
CAG CCT CTG CAG GTT GCT CTG CAC TTG
Gln Pro Leu Gln Val Ala Leu His Leu

1028
CAA CAT AAG CCC AAC CAC ATC AAT TGC
Gln His Lys Pro Asn His Ile Asn Cys

1053
TGC AAA ACA AAA CTA CAG CAT TCT CCA
Cys Lys Thr Lys Leu Gln His Ser Pro

1080
TAC CAC TTA AAT AAG ACA CAG AGT CTC
Tyr His Leu Asn Lys Thr Gln Ser Leu

1107
ACA ACA TTC AAA ACG CCC AGG ACA CAA
Thr Thr Phe Lys Thr Pro Arg Thr Gln

1134
TCC AAA ATT ACT TCT ACA AAA AAT CAG
Ser Lys Ile Thr Ser Thr Lys Asn Gln

1161
GAA AAT CTC AAT GAG CAA GGA AAA TGG
Glu Asn Leu Asn Glu Gln Gly Lys Trp

1188
CAA TCA GTA GCT GCC AGT GCT GAG ATG
Gln Ser Val Ala Ala Ser Ala Glu MET

1215
ACA ATG AGG GTT GGA ATC ATC AAC ATC
Thr MET Arg Val Gly Ile Ile Asn Ile

1248
TTT AAA GTA ATT ATC ATA AGC ATT CTC
Phe Lys Val Ile Ile Ile Ser Ile Leu

1270
CAG CAA GTA ATG GCA AAC ACT CTT GAG
Glu Gln Val MET Ala Asn Thr Leu Glu

1296
ATA AAT GGA AAG ATA AGA AGG CTC AGG
Ile Asn Gly Lys Ile Arg Arg Leu Arg

1323
GAG AAA GTG GAA TGT ACA AAG AAT GAC
Glu Lys Val Glu Cys Thr Lys Asn Asp

1350
CAA GTG GGA ATT GCA CCA CTG GAA ACA
Gln Val Gly Ile Ala Pro Leu Glu Thr

1377
AAT CAC CAG GAT AAA GCA GTC TCT GGC
Asn His Gln Asp Lys Ala Val Ser Gly

1404
TGG GCC AAC AGG AGA ATG GAA ATG AAA
Trp Ala Asn Arg Arg MET Glu MET Lys

1431
AGG GAA AGA GTT GTT ATG GCA GTT GTC
Arg Glu Arg Val Val MET Ala Val Val

1458
CAA TTT GAA CAA CAC AAA AGA CAC
Gln Phe Glu Gln His Lys Arg His .

3. A recombinant DNA molecule comprising:
 i) a vector, and
 ii) said DNA fragment according to claim 1.

4. The recombinant DNA molecule according to claim 3 further comprising a promoter sequence operably linked to said DNA fragment.

5. A host cell transformed with the recombinant DNA molecule according to claim 4.

6. The host cell according to claim 5, wherein said cell is a procaryotic cell.

7. The host cell according to claim 6, wherein said cell is an *E. coli* cell.

8. An isolated DNA fragment coding for the amino acid sequence set forth as follows 81
ATG TTG CCC TTC ACT TGT GGA AGA AAT
MET Leu Pro Phe Thr Cys Gly Arg Asn 108
GCA AAT GAA AAC AGC CCT AGG GAT GTT
Ala Asn Glu Asn Ser Pro Arg Asp Val 135
GAC GTT GGG GTG GCA CCT GCT GCA GAG
Asp Val Gly Val Ala Pro Ala Ala Glu 162
GGT AAC GTG CAG CAT GTC GAG GGC AGC
Gly Asn Val Gln His Val Glu Gly Ser 189
ACT GCC AAG GCT GGT TTG AGC TCA AGG
Thr Ala Lys Ala Gly Leu Ser Ser Arg 216
TCA GGT GGA GGA GGT AGT CTC TCC CAT
Ser Gly Gly Gly Gly Ser Leu Ser His 243
CTC TTC TGC GAG TGC AGC TCT AAA CCC
Leu Phe Cys Glu Cys Ser Ser Lys Pro 270
TGC CTG AAA CAC GTG GAG AAG CTA TCT
Cys Leu Lys His Val Glu Lys Leu Ser 297
GAG CTG CCT CCA GGA CAC ATG CAA ATG
Glu Leu Pro Pro Gly His MET Gln MET 324
GAC ACT CTG ATC ATA AAA TTA TCA GGA
Asp Thr Leu Ile Ile Lys Leu Ser Gly 351
AGA TTG AGA AAT AAG ACA AAA ATG GAG
Arg Leu Arg Asn Lys Thr Lys MET Glu 378
GTG CCA CCA AAC CAG TGG AAA TTT TTC
Val Pro Pro Asn Gln Trp Lys Phe Phe 405
CCC TTT TCA TTC CTC TGG CAT TCC CTG
Pro Phe Ser Phe Leu Trp His Ser Leu 432
GCC TTG ACT CAA GGC AGC CCA CAC TCT
Ala Leu Thr Gln Gly Ser Pro His Ser

```
459
AGG AGC AGA CAC CAG GGC ACA GGT GGG
Arg Ser Arg His Gln Gly Thr Gly Gly

486
GAG CTC TGG GGG ACC CTC CAG GCT TAC
Glu Leu Trp Gly Thr Leu Gln Ala Tyr

513
TCA GTG AAT GGG TTA GCA GCA GCC ACA
Ser Val Asn Gly Leu Ala Ala Ala Thr

540
GGA GCC ACC ATG GAG CCT GCA GGG ACC
Gly Ala Thr MET Glu Pro Ala Gly Thr

567
CAC AAC ACT GAG GGC AGG GAT CTT GCC
His Asn Thr Glu Gly Arg Asp Leu Ala

594
TCT AAT CAG ATA AGC TGT GAT TCC CGA
Ser Asn Gln Ile Ser Cys Asp Ser Arg

621
GAG GGT GGG GTA AAG GCC ACG GGT CTT
Glu Gly Gly Val Lys Ala Thr Gly Leu

648
TTT CTC TCC ACA TCT TCC CAC GTC ATG
Phe Leu Ser Thr Ser Ser His Val MET

675
ACC CCA GAG GGT CGA AGA GGG AGA AAG
Thr Pro Glu Gly Arg Arg Gly Arg Lys

702
TGT GAG CAC CGT GAC ATA ATG AGC CGC
Cys Glu His Arg Asp Ile MET Ser Arg

729
AGC CTT CTG ACT AGA TGC CCC AAA GAA
Ser Leu Leu Thr Arg Cys Pro Lys Glu

756
GAA TCC CAG GTG ACC ACA CAG CAT CAG
Glu Ser Gln Val Thr Thr Gln His Gln

783
AGA AAC TGC AGG GTA ATG AGG AAC TTT
Arg Asn Cys Arg Val MET Arg Asn Phe

810
GGA AAG CAA TCC ATC GTG TTG TCA GTA
Gly Lys Gln Ser Ile Val Leu Ser Val

837
AAA CCT CTG GCT CAC TCC CGA GCT GGG
Lys Pro Leu Ala His Ser Arg Ala Gly

864
CAT GCA TGG ATG GTG ACC CTC GAT GGA
His Ala Trp MET Val Thr Leu Asp Gly

891
ATA GAC TAT GAG GAA CCA GGT GAG GGG
Ile Asp Tyr Glu Glu Pro Gly Glu Gly

918
ATC TAC CTC CAC CGA GAC GTG AGA GTG
Ile Tyr Leu His Arg Asp Val Arg Val

947
ACC TGC ATA CCC AAA CAC CAT GAG GCT
Thr Cys Ile Pro Lys His His Glu Ala

974
TTA AAG ACT GAG CTG ATG TGG AAG CCA
Leu Lys Thr Glu Leu MET Trp Lys Pro

999
CAG CCT CTG CAG GTT GCT CTG CAC TTG
Gln Pro Leu Gln Val Ala Leu His Leu

1028
CAA CAT AAG CCC AAC CAC ATC AAT TGC
Gln His Lys Pro Asn His Ile Asn Cys

1053
TGC AAA ACA AAA CTA CAG CAT TCT CCA
Cys Lys Thr Lys Leu Gln His Ser Pro

1080
TAC CAC TTA AAT AAG ACA CAG AGT CTC
Tyr His Leu Asn Lys Thr Gln Ser Leu

1107
ACA ACA TTC AAA ACG CCC AGG ACA CAA
Thr Thr Phe Lys Thr Pro Arg Thr Gln

1134
TCC AAA ATT ACT TCT ACA AAA AAT CAG
Ser Lys Ile Thr Ser Thr Lys Asn Gln

1161
GAA AAT CTC AAT GAG CAA GGA AAA TGG
Glu Asn Leu Asn Glu Gln Gly Lys Trp

1188
CAA TCA GTA GCT GCC AGT GCT GAG ATG
Gln Ser Val Ala Ala Ser Ala Glu MET

1215
ACA ATG AGG GTT GGA ATC ATC AAC ATC
Thr MET Arg Val Gly Ile Ile Asn Ile

1248
TTT AAA GTA ATT ATC ATA AGC ATT CTC
Phe Lys Val Ile Ile Ile Ser Ile Leu

1270
CAG CAA GTA ATG GCA AAC ACT CTT GAG
Gln Gln Val MET Ala Asn Thr Leu Glu

1296
ATA AAT GGA AAG ATA AGA AGG CTC AGG
Ile Asn Gly Lys Ile Arg Arg Leu Arg

1323
GAG AAA GTG GAA TGT ACA AAG AAT GAC
Glu Lys Val Glu Cys Thr Lys Asn Asp

1350
CAA GTG GGA ATT GCA CCA CTG GAA ACA
Gln Val Gly Ile Ala Pro Leu Glu Thr

1377
AAT CAC CAG GAT AAA GCA GTC TCT GGC
Asn His Gln Asp Lys Ala Val Ser Gly

1404
TGG GCC AAC AGG AGA ATG GAA ATG AAA
Trp Ala Asn Arg Arg MET Glu MET Lys

1431
AGG GAA AGA GTT GTT ATG GCA GTT GTC
Arg Glu Arg Val Val MET Ala Val Val

1458
CAA TTT GAA CAA CAC AAA AGA CAC
Gln Phe Glu Gln His Lys Arg His .

* * * * *
```